United States Patent
Koch et al.

[11] Patent Number: 5,922,244
[45] Date of Patent: Jul. 13, 1999

[54] 4-ACYLAMINOPIPERIDIN-N-OXYLE

[75] Inventors: Andreas Koch, Bobenheim-Roxheim; Alexander Aumüller, Neustadt; Konrad Mitulla, Ludwigshafen; Gregor Tremmel, Grünstadt; Holger Herbst, Frankenthal, all of Germany

[73] Assignee: BASF Aktiengesellschaft, Ludwigshafen, Germany

[21] Appl. No.: 08/913,613

[22] PCT Filed: Mar. 15, 1996

[86] PCT No.: PCT/EP96/01122

§ 371 Date: Sep. 22, 1997

§ 102(e) Date: Sep. 22, 1997

[87] PCT Pub. No.: WO96/29311

PCT Pub. Date: Sep. 26, 1996

[30] Foreign Application Priority Data

Mar. 21, 1995 [DE] Germany .......................... 195 10 184

[51] Int. Cl.$^6$ .......................... C09K 15/20; C07D 211/58
[52] U.S. Cl. .......................... 252/403; 546/186; 546/244
[58] Field of Search ............................ 546/244, 186; 524/99; 252/403

[56] References Cited

FOREIGN PATENT DOCUMENTS

| | | |
|---|---|---|
| A 0 094 048 | 11/1983 | European Pat. Off. . |
| B 0 316 582 | 5/1989 | European Pat. Off. . |
| A 0 581 737 | 2/1994 | European Pat. Off. . |
| A 0 697 386 | 2/1996 | European Pat. Off. . |
| A 1 027 150 | 10/1981 | U.S.S.R. . |
| A 1 139 722 | 4/1983 | U.S.S.R. . |

OTHER PUBLICATIONS

Database Crossfire, Beilstein Informationssyteme GmbH, Frankfurt DE, pp. 1446–1457.
Database Crossfire, Beilstein Informationssyteme GmbH, Frankfurt DE, pp. 207–213.
Database Crossfire, Beilstein Informationssyteme GmbH, Frankfurt DE, p. 2106.
Database Crossfire, Beilstein Informationssyteme GmbH, Frankfurt DE, p. 1100.
Chemical Abstracts, vol. 99, No. 26, Dec. 26, 1983. M.D. Goldfein et al. "Stabilization of Styrene or Methyl Methacrylate", p. 8.
Macromolecules, Bd 23, Nr. 3. Feb. 5, 1990. E.J. Vlietstra et al. Synthesis and Magnetic Properties of a Rigid High Spin Density Polymer with Piperidine–N–Oxyl Pending Groups, p. 946.
Investigative Radiology Bd. 21. Feb. 2, 1986. Richard L. Ehman et al. Diradical Nitroxyl Spin Label contrast Agents for magnetic Resonance Imaging. A Comparison of Relaxation Effectiveness, p. 126.
Journal of the American Chemical Society, Bd. 99. Mar. 2, 1977. Paul Rey et al. Clustering of Nitroxide Spin Labels in Lipid Bilayer Membranes, p. 1638.
Journal of Organic Chemistry, Bd. 56. Oct. 11, 1991. Zhenkun Ma et al. "Organic Oxoammonium Salts. 3.1 A New Convenient Method for the Oxidation of Alcohols to Aldehydes and Ketones", p. 6114.
Bulletin of the Academy of Sciences of the USSR Division of Chemical Science. Feb. 20, 1986. G. N. Bondarev et al. Synthesis of 2,2,6,6–Tetramethyl–4–Diaminoalkylpiperidin–1–Oxyls, p. 1701.
Bulletin of Academy of Sciences of the USSR Division of Chemical Science. Aug. 20, 1986. G. N. Bondarev et al. "Synthesis of 2,2,6,6–Tetramethyl–4–Amino–N–(Alkylmaleimido)–Piperidyl–1–Oxides", pp. 363 and 366.
Bulletin of the Academy of Sciences of the USSR Division of Chemical Science. Jan. 20, 1989. "Synthesis of 2,2,6,6–Tetramethyl–4–Amino–N–(Alkylaminodichlortriazine)–1–Oxylpiperidines" p. 1455.

*Primary Examiner*—Alan L. Rotman
*Assistant Examiner*—Charanjit S. Aulakh
*Attorney, Agent, or Firm*—Oblon, Spivak, McClelland, Maier & Neustadt, P.C.

[57] ABSTRACT

4-Acylaminopiperidine N-oxides Ia $$A^1B^1 \qquad (Ia)$$

where $A^1$ is hydrogen or an organic radical and $B^1$ is a radical IIa

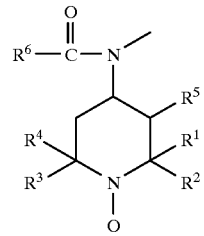

(IIa)

where $R^1$–$R^4$ are each $C_1$–$C_4$-alkyl and $R^1$ and $R^2$, on the one hand, and $R^3$ and $R^4$, on the other hand, may furthermore be bonded to form a 5-membered or 6-membered ring, $R^5$ is H or $C_1$14 $C_4$-alkyl and $R^6$ is H or $C_1$–$C_{18}$-alkyl, are used for stabilizing organic materials against the harmful effect of free radicals, particularly in the distillation of monomers which undergo free radical polymerization, especially styrene.

31 Claims, No Drawings

4-ACYLAMINOPIPERIDIN-N-OXYLE

BACKGROUND OF THE INVENTION

4-Acylaminopiperidine N-oxides

The present invention relates to novel 4-acylaminopiperidine N-oxides of the general formula Ia $$A^1B^1 \quad \text{(Ia)}$$

where $A^1$ is hydrogen or an organic radical and $B^1$ is a radical of the general formula IIa

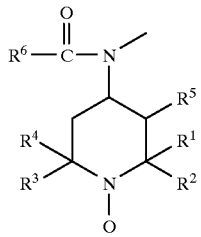

(IIa)

where $R^1$–$R^4$ are each $C_1$–$C_4$-alkyl and $R^1$ and $R^2$, on the one hand, and $R^3$ and $R^4$, on the other hand, may furthermore be bonded to form a 5-membered or 6-membered ring, $R^5$ is H or $C_1$–$C_4$-alkyl and $R^6$ is H or $C_1$–$C_{18}$-alkyl.

The present invention also relates to a process for the preparation of the compounds Ia, the use of the compounds for stabilizing organic materials against the harmful effect of free radicals, in particular of styrene during distillation, the joint use of the compounds Ia or Ib with aromatic nitro or nitroso compounds or substituted phenols, and liquid or solid organic materials which contain the compounds Ia.

Description of the Background

The stabilization of organic materials against damage by free radicals, as formed under the influence of light or heat, is generally known. Compounds from various classes of substances, including the N-oxides of various derivatives of 2,2,6,6-tetramethylated piperidines, have been proposed to date as stabilizers for this purpose.

One compound of this type, which is derived from 4-amino-2,2,6,6-tetramethylpiperidine N-oxide, is the bisamide of adipic acid

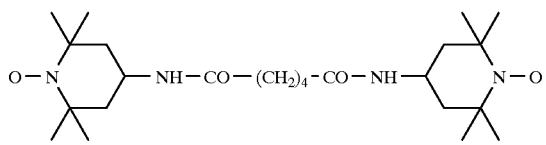

which is described in SU-A 1 139 722. Similar known compounds contain the ester or carbamate group (EP-A 0 581 737 and SU-A 1 027 150, respectively) instead of the carboxamido group.

Furthermore, EP-A 0 581 737 discloses that the stabilizing effect of N-oxides is increased if they are used together with aromatic nitro compounds.

In addition, EP-B 0 316 582 discloses non-free radical piperidine derivatives having the structural unit

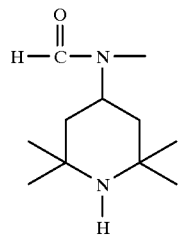

which are suitable as stabilizers for organic material.

SUMMARY OF THE INVENTION

Since the N-oxides known to date have an unsatisfactory action, it is an object of the present invention to provide novel N-oxides having improved performance characteristics.

We have found that this object is achieved by the 4-acylaminopiperidine N-oxides defined at the outset.

We have also found a process for the preparation of the compounds Ia and Ib, the use of these compounds for stabilizing organic materials, their joint use with other stabilizers, and liquid or solid organic materials which contain the compounds Ia or Ib.

DETAILED DESCRIPTION OF THE INVENTION

The structural element of the compounds Ia which is essential for the stabilizing properties is the moiety $B^1$ of the general formula IIa.

In this formula, $R^1$ to $R^4$ may be alkyl, such as methyl, ethyl, propyl or butyl, methyl being particularly preferred. Alicyclic radicals in which $R^1$ and $R^2$ or $R^3$ and $R^4$ together form a tetramethylene or a pentamethylene group are also suitable.

$R^5$ may likewise be alkyl, such as methyl, ethyl, propyl or butyl, but is preferably hydrogen.

Suitable radicals $R^6$ are lower alkyl, such as methyl, ethyl, propyl, butyl or longer-chain radicals of up to 18 carbon atoms. However, $R^6$ is preferably hydrogen, so that in this case the amino group carries a formyl radical.

The moiety $A^1$ serves in particular for adapting the chemical and physical properties of the compounds to the various intended uses. By varying the moiety $A^1$, for example, the solubility in various organic materials, the volatility and the compatibility with other assistants can be influenced.

In addition to being hydrogen, $A^1$ may be, for example, $C_1$–$C_{22}$-alkyl, such as methyl, ethyl, n-propyl, isopropyl, n-butyl, isobutyl, n-pentyl, isopentyl, hexyl, octyl, decyl, dodecyl, octadecyl, pivalyl, 3,3-dimethylbut-2-yl, neopentyl, 4-methylpent-2-yl or 2-ethylhexyl, $C_3$–$C_{22}$-alkenyl, such as allyl, butenyl, pentenyl or oleyl, $C_3$–$C_{12}$-cycloalkyl, such as cyclopropyl, cyclobutyl, cyclopentyl, cyclohexyl, methylcyclohexyl, cycloheptyl, cyclooctyl, cyclododecyl or bicycloheptyl, especially cyclopentyl or cyclohexyl, cyano-, hydroxyl- or carboalkoxy-substituted $C_2$–$C_{22}$-alkyl, such as cyanomethyl, hydroxyethyl, hydroxypropyl, hydroxybutyl, carbomethoxyethyl or carboethoxyethyl, $C_4$–$C_{22}$-alkyl which is interrupted by ether oxygen or nitrogen or substituted by hydroxyl, such as —(CH$_2$)

$_3N(CH_3)_2$, $-(CH_2)_3N(C_2H_5)_2$, $-(CH_2)_3-OCH_3$, $-(CH_2)_3-O-CH(CH_3)_2$, $-(CH_2)_2O\ (CH_2)_2-OH$, $-CH_2-(CH_2)_2-CH_2-N(CH_3)_3$, $-(CH_2)_2-N[CH(CH_3)_2]_2$, $-(CH_2)_2-N(C_2H_5)_2$, $-(CH_2)_2N(CH_3)_2$, $-(CH_2)_2O\ CH_3$ or $-(CH_2)_2OCH_2CH_3$, substituted $C_7-C_{22}$-phenyl and $C_{13}-C_{22}$-diphenylalkyl radicals, such as benzyl, the isomeric methoxybenzyls, methylbenzyls, ethylbenzyls, isopropylbenzyls, trimethylbenzyls, fluorobenzyls, chlorobenzyls, methylenedioxybenzyls, phenylethyls, phenylpropyls and phenylbutyls, dimethylaminobenzyls, diphenylmethyl and 1,3-diphenylprop-2-yl, aryl, such as phenyl, tolyl or carbo-$C_1$-$C_4$-alkoxy-substituted phenyl, $C_1-C_{22}$-alkyl carrying a heterocyclic structure eg.

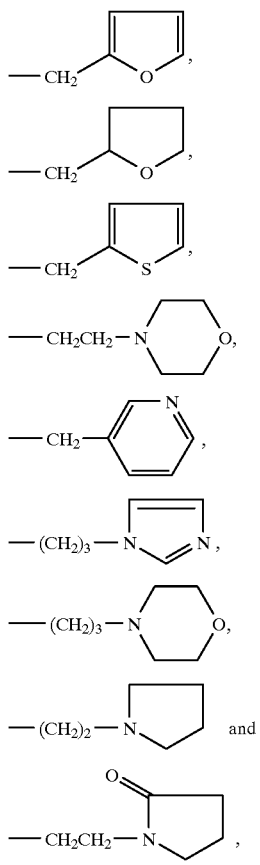

a phosphorus-containing group, such as a phosphoramide, a phosphinic acid derivative or a phosphoric acid derivative having alkyl radicals or a nitrogen- and/or oxygen-containing organic radicals of an aliphatic, aromatic or heterocyclic nature.

Preferred compounds Ia are those in which $A^1$ in turn carries further radicals IIa. Consequently, on the one hand the compounds attain a molecular weight which greatly reduces their volatility and on the other hand the presence of two active stabilizer groups increases the stabilizing effect of the compounds. Among the compounds of the formula Ia, in particular the compounds of the formula Ib have these properties.

In addition to the moieties IIa, the compounds Ib may also contain moieties IIb in which $R^7$ may be hydrogen, hydroxyl or a C— or O-organic radical. In particular, formyl, O-alkyl, O-aryl, O-hydrocarbyl, O-carbamoyl, cyanomethyl or substituted alkenyl may serve as such radicals. The possibilities and preferences which apply to $R^1$ to $R^6$ are the same as those stated for the moieties IIa.

Examples of suitable moieties $A^2$ are the following radicals:

$C_2-C_{22}$-alkylene and $C_5-C_{22}$-cycloalkylene, such as $-(CH_2)_p-CH_2-$ (where p is 1 to 21)

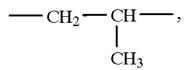

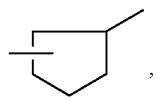

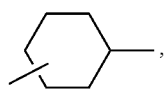

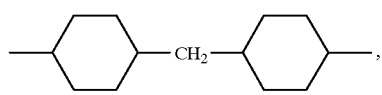

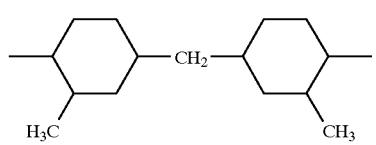

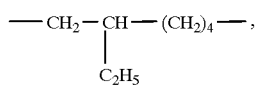

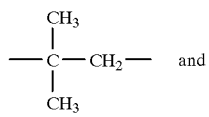

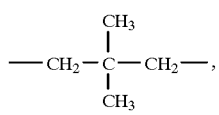

$C_8-C_{14}$-phenylalkylene and phenylene, such as

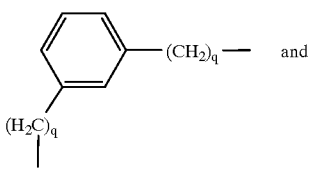

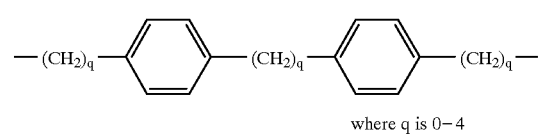

where q is 0–4 alkylene which is interrupted by ether oxygen, nitrogen or heterocyclic structures, such as $-(CH_2)_3O(CH_2)_4O(CH_2)_3-$, $-(CH_2)_3O(CH_2)_2O(CH_2)_2O(CH_2)_3-$,

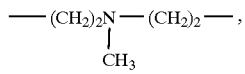

-continued
—(C₃H₆O)ᵣ—C₃H₆—  where r is 1 to 33,
—(CH₂)₃N—(CH₂)₃—,
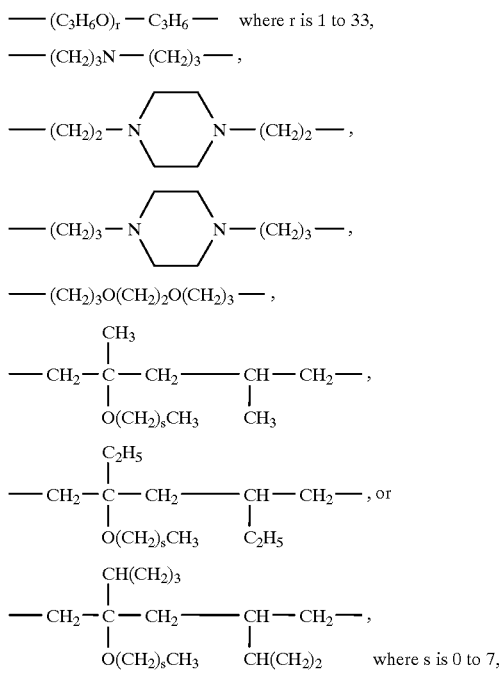
where s is 0 to 7,
carbon-, oxygen- and/or nitrogen-containing bridges having phosphorus as a heteroatom, such as
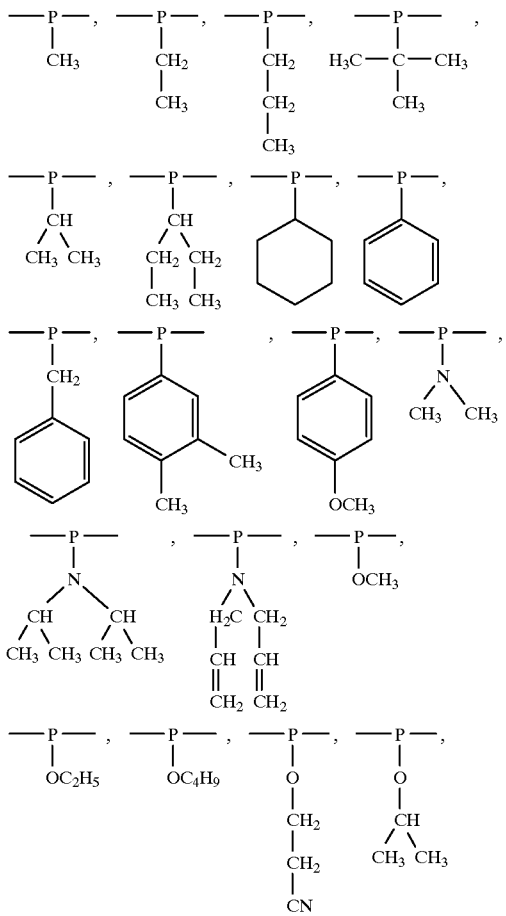
-continued
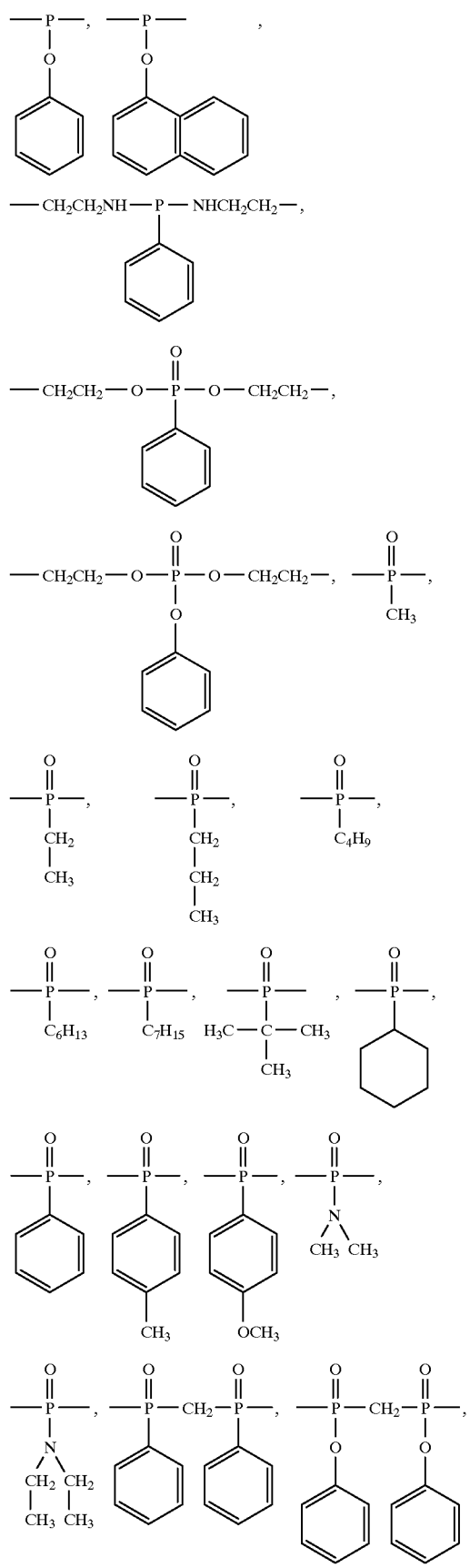

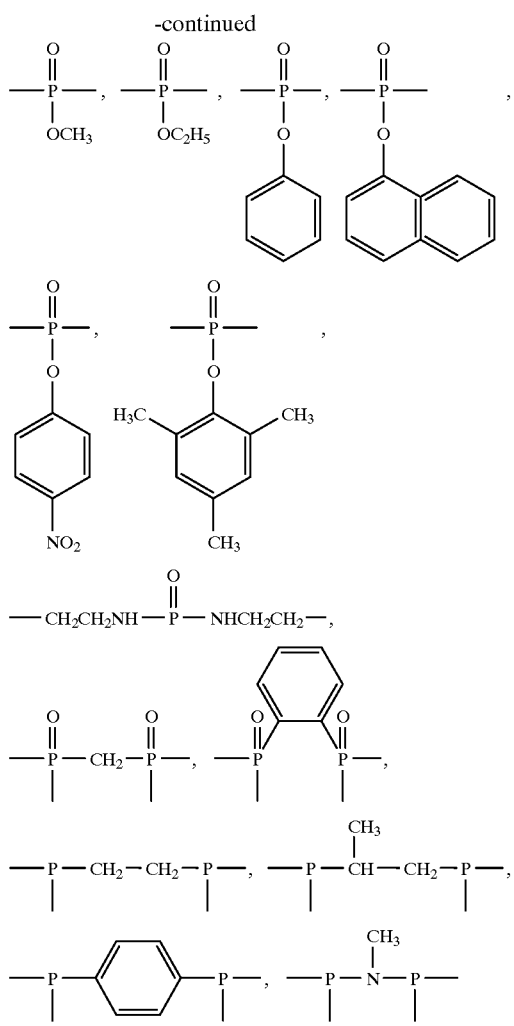

Particularly preferred compounds are compounds of the formula Ib in which all moieties $B^2$ are N-oxylpiperidine radicals and the moiety $A^2$ is short-chain alkylene of 2 to 8 carbon atoms, such as —$CH_2$—$CH_2$—, —$(CH_2)_4$—, —$(CH_2)_6$— or —$(CH_2)_8$—.

The novel compounds can be prepared by oxidation of the corresponding piperidine compounds with hydrogen peroxide. The piperidine compounds used and their preparation are described, for example, in EP-A 0 316 582 or can be prepared in a known manner. The oxidation reaction is preferably carried out with the addition of organic solvents.

Preferably used organic solvents are those which are at least partially miscible with water, for example polar protic solvents, such as alcohols, in particular methanol, ethanol, propanol, n-butanol and isobutanol, and polar aprotic solvents, such as dimethylformamide, dimethylacetamide, N-methylpyrrolidone and tetrahydrothiophene dioxide.

The oxidation is preferably carried out at a pH of from 6.5 to 11, particularly preferably from 7.0 to 8.5, very particularly preferably from 7.5 to 8.0, and the pH can be brought to the desired value and can be kept constant by the presence of buffer compounds, such as sodium carbonate, sodium bicarbonate, potassium or sodium mono- or dihydrogen phosphate, or sodium or potassium bisulfate, or organic acids, such as acetic acid, formic acid, cyanoacetic acid, malonic acid or lactic acid. Inorganic acids, such as hydrochloric acid, sulfuric acid or phosphoric acid, and inorganic bases, such as sodium hydroxide, lithium hydroxide or, particularly preferably, potassium hydroxide, which may be used in the form of an aqueous or alcoholic solution, are also suitable for adjusting the pH.

The presence of catalytic amounts of oxides, hydroxides or salts of magnesium, of calcium or of zinc is also advantageous, suitable anions being chloride, bromide, sulfate and phosphate. Good results are obtained, for example, with magnesium sulfate. Boric acid, salts thereof and hydrates of these salts can also advantageously be used as catalysts. The concentration of the salts is from 0.01 to 10, preferably 0.1, mol %, based on the amount of acylaminopiperidine.

The oxidation is preferably carried out at from 40 to 100° C., in particular from 60 to 80° C. After reaction times of from 0.5 to about 24 hours, the reaction mixture is advantageously cooled to room temperature, water is added and the resulting reaction products are separated off in a manner known per se in the form of solids. Particularly in the case of reactions which are carried out in the presence of readily volatile solvents, for example methanol, ethanol or isopropanol, the reaction mixture can be worked up by removing the solvent by distillation with or without the addition of water. The oxidation conditions are so mild and selective that there is no elimination of sensitive groups, for example of the acyl radical $R^6$—CO—. After the oxidation has ended, it is advantageous to decompose excess hydrogen peroxide. This can be done, for example, by treating the reaction mixture with iron or manganese salts, preferably iron(II) sulfate, at slightly alkaline pH, eg. at pH 9–10.

It is not essential for the oxidation reaction to go to completion. Even the partially oxidized piperidine compounds have good activity.

The novel 4-acylaminopiperidine N-oxides are suitable for stabilizing organic materials and protect them from the harmful effect of light and heat. The organic materials which can be stabilized by the compounds include plastics of all types, for example polypropylene, polyethylene, acrylonitrile/butadiene/styrene copolymers, polyamides, polyurethanes and pigment-containing polyolefins. Fats, oils and surface coatings can also be stabilized with the novel compounds.

Stabilizers Ia and Ib are particularly advantageous for stabilizing monomers which undergo free radical polymerization, such as the esters and amides of acrylic acid and methacrylic acid as well as these acids themselves, acrylonitrile, methacrylonitrile, vinyl chloride and styrene.

The novel compounds can advantageously be used in particular for stabilization during storage and during distillation. The novel compounds Ia and Ib are particularly important in the distillation of styrene, which is sensitive to polymerization.

The novel compounds Ia and Ib, particularly those in which $R^6$ is hydrogen, have a very good stabilizing effect per se. This effect can often be increased further by combination with aromatic nitro or nitroso compounds or with substituted phenols. Examples of aromatic nitro compounds which may be used are
1,3-dinitrobenzene,
1,4-dinitrobenzene,
2,6-dinitro-4-methylphenol,
2-nitro-4-methylphenol,
2,4,6-trinitrophenol,
2,4-dinitro-1-naphthol,
2,4-dinitro-6-methylphenol,
2,4-dinitrochlorobenzene,
2,4-dinitrophenol, 2,4-dinitro-6-sec-butylphenol,
4-cyano-2-nitrophenol,
3-iodo-4-cyano-5-nitrophenol,
particularly preferably 2,6-dinitro-4-methylphenol,
2-nitro-4-methylphenol,
2,4-dinitro-6-sec-butylphenol and
2,4-dinitro-6-methylphenol.

Examples of suitable aromatic nitroso compounds are
p-nitrosophenol,
p-nitroso-o-cresol and
p-nitroso-N,N-diethylaniline.

Examples of suitable substituted phenols are:
4-tert-butylpyrocatechol,
methoxyhydroquinone,
2,6-di-tert-butyl-4-methylphenol,
n-octadecyl-β-(3,5-di-tert-butyl-4-hydroxyphenyl) propionate,
1,1,3-tris(2-methyl-4-hydroxy-5-tert-butylphenyl)butane,
1,3,5-trimethyl-2,4,6-tris(3,5-di-tert-butyl-4-hydroxybenzyl)benzene,
1,3,5-tris(3,5-di-tert-butyl-4-hydroxybenzyl) isocyanurate,
1,3,5-tris[β-(3,5-di-tert-butyl-4-hydroxyphenyl) propionyloxyethyl] isocyanurate,
1,3,5-tris(2,6-dimethyl-3-hydroxy-4-tert-butylbenzyl) isocyanurate and
pentaerythrityl tetrakis[β-(3,5-di-tert-butyl-4-hydroxyphenyl)propionate].

The 4-acylaminopiperidine N-oxides Ia and Ib can, if desired, also be used in any desired combination with other N-oxides, for example with
di-tert-butyl-nitroxyl,
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl) adipinamide,
N-(1-oxyl-2,2,6,6-tetramethylpiperidin-4-yl)caprolactam,
N-(1-oxyl-2,2,6,6-tetramethylpiperidin-4-yl) dodecylsuccinimide,
2,4,6-tris[N-butyl-N-(1-oxyl-2,2,6,6-tetramethylpiperidin-4-yl]-s-triazine and
4,4'-ethylenbis(1-oxyl-2,2,6,6-tetramethylpiperazin-3-one).

Combination with sterically hindered amines, such as 2,2,6,6-tetramethylpiperidine derivatives, is also advantageous. These include the nonoxidized starting compounds for the novel compounds.

In all cases, up to 50% by weight of Ia or Ib can be replaced by other oxyl compounds.

For stabilization purposes, the novel compounds are preferably used in the following concentrations:

For the stabilization of plastics:
  Ia or Ib alone: from 0.01 to 5, preferably from 0.02 to 1, % by weight, based on the amount of plastic.

For the stabilization of fats, oils and surface coatings:
  from 0.01 to 5, preferably from 0.02 to 1, % by weight.

For the storage of monomers which undergo free radical polymerization:
  from 0.0002 to 0.1, preferably from 0.0005 to 0.01, % by weight.

For the distillation of monomers which undergo free radical polymerization:
  from 0.0005 to 0.5, preferably from 0.005 to 0.05, % by weight.

Ia or Ib in combination with an aromatic nitro or nitroso compound or with a substituted phenol as costabilizer:
  from 0.0005 to 0.5, preferably from 0.005 to 0.05, % by weight of Ia or Ib plus from 0.001 to 0.5% by weight of costabilizer.

EXAMPLES

Example 1

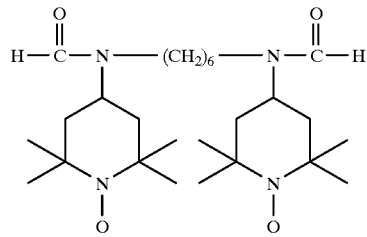

600 ml of a 30% strength by weight solution of hydrogen peroxide (19.6 mol) were added to a suspension of 540 g (1.37 mol) of N,N'-bis[2,2,6,6-tetramethylpiperidin-4-yl]-N,N'-bisformyl-1,6-diaminohexane, 800 ml of water, 150 ml of isobutanol and 200 mg of MgSO$_4$ at 70° C. in the course of 2 hours, and the mixture was then kept at this temperature for a further 16 hours. The mixture was then cooled to room temperature and the precipitated product was isolated in the usual manner. The product contains not only the di-N-oxide but also the mono-N-oxide compound as a byproduct.

Yield: 85%, melting point: from 169 to 170° C.

In a similar way to Example 1 but using methanol instead of water/isobutanol as the solvent, the following examples of compounds were prepared:

| Ex. | Starting material | Product | Yield | Melting point |
|---|---|---|---|---|
| 2 | OHC-N-butyl-2,2,6,6-tetramethylpiperidine (NH) | OHC-N-butyl-2,2,6,6-tetramethylpiperidine (N-O) | 98.0% of theory | 70° C. |
| 3 | OHC-N-benzyl-2,2,6,6-tetramethylpiperidine (NH) | OHC-N-benzyl-2,2,6,6-tetramethylpiperidine (N-O) | 78.0% of theory | 118° C. |
| 4 | bis-piperidinyl compound (NH) | bis-piperidinyl compound (N-O) | 88.5% of theory | 212° C. |

Example 5

Stabilizing effect of the compound according to Example 1 in styrene:

The stabilizer according to Example 1 and, for comparison, various conventional stabilizers were dissolved in a concentration of 120 ppm in styrene. 500 ml of this solution were heated to 110° C. under nitrogen in a reaction vessel. 250 g/hour of an identical solution were metered continuously into this heated styrene solution and the same amount was removed continuously. The equilibrium polymer content was measured at the outlet. The following results were found:

| Stabilizer | Polymer content in % |
|---|---|
| According to the invention: | 0.10 |
| Compound according to Example 1 | |
| For comparison: | |
| Bis(1-oxyl-2,2,6,6-tetramethyl-piperidin-4-yl) sebacate | 0.24 |
| p-Nitrosophenol | 0.18 |
| p-Nitroso-o-cresol | 0.30 |
| Without stabilizer: | >5.00* |

*termination before equilibrium was established

Example 6

Stabilizing effect of the compound according to Example 1 in combination with a costabilizer:

The stabilizer according to Example 1 and, for comparison, a conventional stabilizer were dissolved in a concentration of 120 ppm in styrene. In addition, 2,4-dinitro-sec-butylphenol, as a costabilizer, was dissolved in a concentration of 240 ppm in this styrene. The solutions were subjected to a test as in Example 5, and once again the polymer content was measured at the outlet. The following results were found:

| Stabilizer | Polymer content in % |
|---|---|
| According to the invention: | 0.04 |
| Compound according to Example 1 + 2,4-dinitro-sec-butylphenol | |
| For comparison: | 0.07 |
| Bis(1-oxyl-2,2,6,6-tetramethyl-piperidin-4-yl) sebacate + 2,4-dinitro-sec-butylphenol | |

Example 7

Stabilizing effect of the compound according to Example 1 in acrylic acid:

Acrylic acid was melted in an ampoule with the addition of 50 ppm of the stabilizer according to Example 1 and, for comparison, various conventional stabilizers, and the melt was thermostated at 80° C. The induction period to the beginning of polymerization was measured. The following results were found:

| Stabilizer | Induction period [h] |
|---|---|
| According to the invention: | |
| Compound according to Example 1 | 502 |
| For comparison: | |
| Bis(1-oxyl-2,2,6,6-tetramethyl-piperidin-4-yl) sebacate | 470 |
| Phenothiazine | 170 |
| Without stabilizer: | 1 |

We claim:

1. A 4-acylaminopiperidine N-oxide of the formula Ia $$A^1B^1 \quad \text{(Ia)}$$

where $A^1$ is an organic radical selected from the group consisting of alkyl, alkenyl, cycloalkyl, cyano-substituted, hydroxyl-substituted, or carboalkoxy-substituted alkyl, alkyl which is interrupted by ether oxygen or nitrogen or substituted by hydroxyl, substituted $C_{7-22}$-phenyl and $C_{13-22}$-diphenylalkyl, aryl, carbo-$C_1$–$C_4$-alkoxy-substituted phenyl,

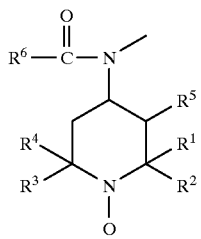

(IIa)

$C_{1-22}$-alkyl substituted with a heterocyclic structure and a phosphorous-containing group, and $B^1$ is a radical of the formula IIa where:

$R^1$–$R^4$ are each $C_1$–$C_4$-alkyl and $R^1$ and $R^2$, on the one hand, and $R^3$ and $R^4$, on the other hand, may furthermore be bonded to form a 5-membered or 6-membered ring, $R^5$ is H or $C_1$–$C_4$-alkyl and $R^6$ is H.

2. A 4-acylaminopiperidine N-oxide of the formula Ib $$A^2(B^2)_n \quad \text{(Ib)}$$

where $A^2$ is an n-valent organic radical selected from the group consisting of alkylene, cycloalkene, phenylalkylene, phenylene, alkylene which is interrupted by ether oxygen or nitrogen or heterocyclic structures, and carbon-, oxygen- and/or nitrogen-containing bridges having phosphorus as a heteroatom, n is from 2 to 4 and at least one of the radicals $B^2$ is a radical IIa and the remaining radicals $B^2$ are identical or different radicals of the formula IIb

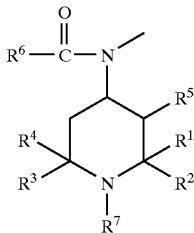

(IIb)

where $R^1$–$R^6$ are as defined above and $R^7$ is hydrogen, hydroxyl, formyl, O-alkyl, O-aryl, O-hydrocarbyl, O-carbamoyl, cyanomethyl and substituted alkenyl.

3. A 4-acylaminopiperidine N-oxide as claimed in claim 1 in which $R^5$ and $R^6$ are each hydrogen.

4. A 4-acylaminopiperidine N-oxide as claimed in claim 1 in which $R^1$ to $R^4$ are each methyl.

5. A 4-acylaminopiperidine N-oxide as claimed in claim 2 in which $A^2$ is α,ω-alkylene of 2 to 8 carbon atoms.

6. N,N'-Bis(1-oxyl-2,2,6,6-tetramethylpiperidin-4-yl)-N,N'-bisformyl-1,6-diaminohexane.

7. A process for the preparation of a 4-acylaminopiperidine N-oxide as claimed in claim 4 wherein the corresponding N-unsubstituted piperidine is oxidized with hydrogen peroxide.

8. A process for the purification of monomers which undergo free radical polymerization by distillation of the contaminated monomers, wherein the distillation is carried out in the presence of a 4-acylaminopiperidine N-oxide as claimed in claim 1.

9. A process as claimed in claim 8, which is used for the purification of styrene.

10. A mixture of 4-acylaminopiperidine N-oxide as claimed in claim 1 and an aromatic nitro or nitroso compound or substituted phenol.

11. A liquid or solid organic material containing a 4-acylaminopiperidine N-oxide as claimed in claim 1.

12. A 4-acylaminopiperidine-N-oxide as claimed in claim 2, wherein $R^5$ and $R^6$ are each hydrogen.

13. A 4-acylaminopiperidine-N-oxide as claimed in claim 2, wherein $R^1$, $R^2$, $R^3$ and $R^4$ are each methyl.

14. A process for the preparation of a 4-acylaminopiperidine-N-oxide as claimed in claim 2, wherein the corresponding N-unsubstituted piperidine is oxidized with hydrogen peroxide.

15. A process for purifying contaminated monomers which undergo free radical polymerization, comprising distilling the contaminated monomers in the presence of a 4-acylaminopiperidine-N-oxide as claimed in claim 2.

16. A mixture comprising (a) a 4-acylaminopiperdine-N-oxide as claimed in claim 2 and (b) at least one member selected from the group consisting of an aromatic nitro compound, an aromatic nitroso compound and a substituted phenol.

17. A liquid or solid organic material comprising a 4-acylaminopiperdine-N-oxide as claimed in claim 2.

18. A method of stabilizing organic materials against the harmful effects of free radicals, comprising combining an organic material with a composition comprising a 4-acylaminopiperdine-N-oxide as claimed in claim 1.

19. The method of claim 18, wherein the composition further comprises at least one member selected from the group consisting of an aromatic nitro compound, an aromatic nitroso compound, a substituted phenol and mixtures thereof.

20. A method of stabilizing organic materials against the harmful effects of free radicals, comprising combining an organic material with a composition comprising a 4-acylaminopiperdine-N-oxide as claimed in claim 2.

21. The method of claim 20, wherein the composition further comprises at least one member selected from the group consisting of an aromatic nitro compound, an aromatic nitroso compound, a substituted phenol and mixtures thereof.

22. A method of stabilizing monomers which undergo free radical polymerization, comprising combining at least one monomer which undergoes free radical polymerization with a composition comprising a 4-acylaminopiperdine-N-oxide as claimed in claim 1.

23. The method of claim 22, wherein the composition further comprises at least one member selected from the group consisting of an aromatic nitro compound, an aromatic nitroso compound, a substituted phenol and mixtures thereof.

24. A method of stabilizing monomers which undergo free radical polymerization, comprising combining at least one monomer which undergoes free radical polymerization with a composition comprising a 4-acylaminopiperdine-N-oxide as claimed in claim 2.

25. The method of claim 24, wherein the composition further comprises at least one member selected from the group consisting of an aromatic nitro compound, an aromatic nitroso compound, a substituted phenol and mixtures thereof.

26. A method of stabilizing styrene comprising combining styrene with a composition comprising a 4-acylaminopiperdine-N-oxide as claimed in claim 1.

27. The method of claim 26, wherein the composition further comprises at least one member selected from the group consisting of an aromatic nitro compound, an aromatic nitroso compound, a substituted phenol and mixtures thereof.

28. A method of stabilizing styrene comprising combining styrene with a composition comprising a 4-acylaminopiperdine-N-oxide as claimed in claim 2.

29. The method of claim 28, wherein the composition further comprises at least one member selected from the group consisting of an aromatic nitro compound, an aromatic nitroso compound, a substituted phenol and mixtures thereof.

30. A compound according to claim 2, wherein n=2, each of the radicals $B^2$ is of the formula (IIa) and $A^2$ is alkylene of 2 to 8 carbon atoms.

31. A compound according to claim 2, wherein n=2, one of the radicals $B^2$ is of the formula (IIa) and the other $B^2$ radical is of the formula (IIb), $R^7$ is H and $A^2$ is alkylene of 2 to 8 carbon atoms.

* * * * *